United States Patent [19]

McLuckey et al.

[11] Patent Number: 4,849,628

[45] Date of Patent: Jul. 18, 1989

[54] ATMOSPHERIC SAMPLING GLOW DISCHARGE IONIZATION SOURCE

[75] Inventors: Scott A. McLuckey; Gary L. Glish, both of Oak Ridge, Tenn.

[73] Assignee: Martin Marietta Energy Systems, Inc., Oak Ridge, Tenn.

[21] Appl. No.: 267,671

[22] Filed: Nov. 4, 1988

Related U.S. Application Data

[63] Continuation of Ser. No. 55,277, May 29, 1987, abandoned.

[51] Int. Cl.$^4$ .................. B01D 59/44; H01J 41/00
[52] U.S. Cl. ......................... 250/282; 250/423 R; 250/288; 250/423 F
[58] Field of Search ............... 250/288, 289, 423 R, 250/423 F, 426, 282

[56] References Cited

U.S. PATENT DOCUMENTS

3,949,230  4/1976  Bach ............................. 250/423 R
4,137,750  2/1979  French et al. ..................... 250/288

OTHER PUBLICATIONS

Carroll et al., "Atmospheric Pressure Ionization Mass Spectrometry", *Applied Spectroscopy Reviews*, vol. 17, #3, pp. 337–406 (1981).
Bruhn et al., "Simplified Solids Mass Spectrometer Combining . . . ", *Analytical Chemistry*, vol. 50, #2, pp. 373–375 (Feb. 1978).
Loving et al., "Simultaneous Analysis of an Abnormal Glow . . . ", *Analytical Chemistry*, vol. 55, #9, pp. 1523–1526 (Aug. 1983).
Loving et al., "Dual-Pin Cathode Geometry for Glow Discharge . . . ", *Analytical Chemistry*, vol. 55, #9, pp. 1526–1530 (Aug. 1983).
Harrison et al., "Glow Discharge Mass Spectrometry", *Analytical Chemistry*, vol. 58, #2, pp. 341A–356A (Feb. 1986).
Carroll et al., "Application of Atmospheric Pressure Ionization . . . ", 23 Ann. Conf. on Mass Spectrometry and Applied Topics, Houston, Texas, May 25–30, 1975.
Reid et al., "Atmospheric Pressure Chemical Ionization Studies . . . ", 24 Ann. Conf. on Mass Spectrometry and Allied Topics, San Diego, California, May 9–13, 1976.
Brochure: "The VG9000 Glow Discharge Mass Spectrometer".

*Primary Examiner*—Bruce C. Anderson
*Attorney, Agent, or Firm*—Joseph A. Marasco; Bruce M. Winchell

[57] ABSTRACT

An atmospheric sampling glow discharge ionization source that can be used in combination with an analytical instrument which operates at high vacuum, such as a mass spectrometer. The atmospheric sampling glow discharge ionization source comprises a chamber with at least one pair of electrodes disposed therein, an inlet for a gaseous sample to be analyzed and an outlet communicating with an analyzer which operates at subatmospheric pressure. The ionization chamber is maintained at a pressure below atmospheric pressure, and a voltage difference is applied across the electrodes to induce a glow discharge between the electrodes, so that molecules passing through the inlet are ionized by the glow discharge and directed into the analyzer. The ionization source accepts the sample under atmospheric pressure conditions and processes it directly into the high vacuum instrument, bridging the pressure gap and drawing off unwanted atmospheric gases. The invention also includes a method for analyzing a gaseous sample using the glow discharge ionization source described above.

20 Claims, 3 Drawing Sheets

ATMOSPHERIC SAMPLING GLOW DISCHARGE IONIZATION SOURCE

The U.S. Government has rights in this invention pursuant to contract No. DE-AC05-840R21400 awarded by U.S. Department of Energy contract with Martin Marietta Energy Systems, Inc.

This application is a continuation of application Ser. No. 055,277 filed May 29, 1987, abandoned.

BACKGROUND OF THE INVENTION

This invention relates to a glow discharge ionization source. More particularly, this invention relates to a glow discharge ionization source which operates at subatmospheric pressure and can directly accept a gaseous sample contained in ambient air. The invention relates specifically to apparatus and a method for detecting and analyzing a gaseous substance in an atmospheric sample.

Prior art systems have had the serious disadvantage of either requiring very large pumping systems and frequent maintenance or having low sensitivity and frequent clogging of the interface between the ion source and mass spectrometer. Since mass spectrometers operate under a high vacuum, it is difficult to obtain a sample of air which includes sufficient molecules of interest to detect without including a vast amount of unwanted atmospheric gases. Furthermore, it is also difficult to obtain indiscriminate ionization with prior art atmospheric ionization devices.

Attempts at analyzing dilute gas samples have produced unsatisfactory results. In atmospheric pressure ionization (API) sources, true thermal and chemical equilibria are obtained, so that only the most thermodynamically stable ions are observed. The less stable ions are, therefore, discriminated against severely. The relatively high operating pressure of the API source increases the probability of ion-ion recombination, which is a major loss mechanism, and also tends to increase the amount of clustering. Additionally, API sources are limited by either the amount of primary ionizing electrons, or the lifetime of the needle that produces the ionizing electrons. The former limitation leads to ionization saturation at relatively high sample concentrations, and discrimination in ionization when two components are present in widely varying concentrations. The kinetics of ion formation also contribute to ion discrimination. The limited lifetime of the needle that produces ionizing electrons precludes using this type of source for routine, continuous long-term applications.

In using an API source, the sample material passes through a region where ionizing electrons are generated. The ionizing electrons can be generated either by beta particle emission from a suitable material (e.g. $^{63}$Ni or $^{3}$H) or by establishing a corona discharge between two electrodes, one of which is a needle. After interacting with the ionizing electrons, the ionized molecules and their charged products are directed into a mass analyzer.

The corona discharge, which occurs at atmospheric pressure, cannot operate for long periods of time before maintenance is required. The discharge needle must be replaced every twenty-four to forty-eight hours due to burnout. This is a disadvantage for both remote monitoring systems and continuously operating systems.

Moreover, conventional API sources use small apertures which increase the chance of aperture clogging and require the use of a complex "gas curtain." In this regard, U.S. Pat. No. 4,137,750 to French et al. discloses an apparatus for analyzing trace components using a gas curtain. The gas curtain is established between a sample gas reaction chamber and a mass analyzer. A sample gas containing trace components is ionized in the reaction chamber which is maintained at atmospheric pressure. The ionized trace components are caused to migrate through the gas curtain by an electric field and separated from the sample gas. The gas curtain must be maintained at a pressure above atmospheric pressure so that no sample gas leaks into the mass analyzer.

Additionally, in the prior art the sensitivity of an API source using a beta emitter has not been adequate for trace atmospheric gas sampling. This is due to the radioactive nature of the beta emitter, which limits the amount that can safely be handled and thus, the number of ionizing electrons.

A different ionization source, chemical ionization (CI), operates at subatmospheric pressure but also requires frequent rebuilding of the electron source, as noted with the corona discharge API source. CI is primarily used for organic chemical analysis and is not used for direct atmospheric sampling.

Glow discharge ionization sources for mass spectrometers have heretofore been used only for inorganic chemical analysis. Typically, it is required that an electrode be made of a solid sample, such as a solid inorganic substance. Examples of conventional ion source electrode configurations are illustrated in W. W. Harrison et al., "Glow Discharge Mass Spectrometry," Analytical Chemistry, Volume 58, No. 2, pages 341A to 356A, February, 1986.

There is a need in the art for an ionization source for use with an atmospheric gas sampling instrument having high sensitivity and reduced tendency to discriminate against less stable ions. In addition, there is a need for a portable monitoring system that can operate in remote areas for extended periods of time before maintenance is required. There is also a need for an ionization source which can accept a gaseous sample directly from the environment and operate at subatmospheric pressure.

SUMMARY OF THE INVENTION

It is therefore an object of the present invention to provide an ionization chamber for gaseous samples for use with a mass spectrometer or other analytical device which analyzes charged particles.

It is a further object of the present invention to provide means for ionizing substances to be analyzed in the presence of normal atmospheric gases.

Another object of the invention is to provide means for producing both positive and negative ions for analysis.

Yet another object of the present invention is to provide a device for ionizing gaseous samples directly from ambient air that operates at a pressure below atmospheric pressure.

These and other objects of the invention are achieved by providing apparatus for analyzing gaseous chemicals in the atmosphere comprising an ionization chamber and an analyzer which analyzes charged particles, said ionization chamber defining an inlet for a gaseous sample to be analyzed and an outlet communicating with said analyzer, at least one pair of spaced electrodes disposed in said chamber proximate to a sample path leading from said inlet to said outlet, means for establishing a glow discharge between said electrodes and means for maintaining said chamber at a pressure below atmospheric pressure.

According to another aspect of the invention, the objects are achieved by providing a method for analyzing gaseous chemicals in the atmosphere comprising the steps of:

(a) providing an ionization chamber defining an inlet for a gaseous sample to be analyzed and an outlet communicating with an analyzer which analyzes charged particles, said chamber having disposed therein at least one pair of spaced electrodes proximate to a sample path leading from said inlet to said outlet;

(b) maintaining the interior of said ionization chamber at subatmospheric pressure;

(c) applying a voltage difference across said electrodes to induce a glow discharge between said electrodes;

(d) admitting a gas sample containing molecules to be analyzed through said inlet into said chamber, ionizing said molecules to be analyzed in said glow discharge, and directing the ionized molecules through the outlet and into the analyzer; and (e) analyzing the ionized molecules in said analyzer.

BRIEF DESCRIPTION OF THE DRAWINGS

Other objects, features and advantages of the present invention will become apparent from the following detailed description and accompanying drawings, wherein.

DETAILED DESCRIPTION OF PREFERRED EMBODIMENTS

The present invention is an ionization chamber for use with mass spectrometry and other ion analysis instruments. The invention comprises an atmospheric sampling glow discharge ionization source used in combination with an analytical instrument. The ionization source comprises a glow discharge ionization chamber having spaced electrodes disposed therein, an inlet communicating with a source of a gaseous sample to be analyzed and an outlet communicating with an analyzer. The chamber is maintained at a pressure below atmospheric pressure. Molecules passing through the inlet and contacting the glow discharge are ionized and directed through the outlet to the analyzer.

The ionization source accepts the sample directly from atmospheric pressure conditions and processes the sample directly into a high vacuum instrument, bridging the pressure gap and drawing off unwanted atmospheric gases. The atmospheric sampling glow discharge ionization source exhibits improved sensitivity and reduced discrimination against less stable ion species in the ionization of trace vapors in ambient air in real time. The improved sensitivity and reduced discrimination of this ionization source compared to other sources make mass spectrometry a more widely applicable technique for detection and identification of gaseous chemicals, particularly organic molecules, in the atmosphere.

Ions are formed by a variety of mechanisms. Positive ions are formed by electron impact near the cathode, whereby the positive ions strike the cathode and liberate other electrons thus sustaining the discharge. The phenomena of glow discharge is well-known and has been extensively studied. Conventional glow discharge technology is described in S. C. Brown, "Introduction To Electrical Discharges and Gases," John Wiley & Sons, Inc., New York, 1966, and W. W. Harrison et al., "Glow Discharge Mass Spectrometry," Analytical Chemistry, Volume 58, No. 2, pages 341A to 356A, February, 1986, which are hereby incorporated herein by reference.

The present invention is directed to apparatus capable of forming ions from trace contaminants in air. The trace contaminant molecules can be predominantly ionized by either electron or proton transfer from ions of much greater abundance, which are commonly referred to as reagent ions. In ambient air, positive reagent ions include $O_2^+$, hydronium ion (protonated water), and protonated water clusters $(H_2O)_nH^+$ where $n \leq 5$. Major negatively charged reagent ions include $O_2^-$ and water adducts of the form $O_2(H_2O)_n^-$ where n is 1, 2, or 3.

Figure 1:
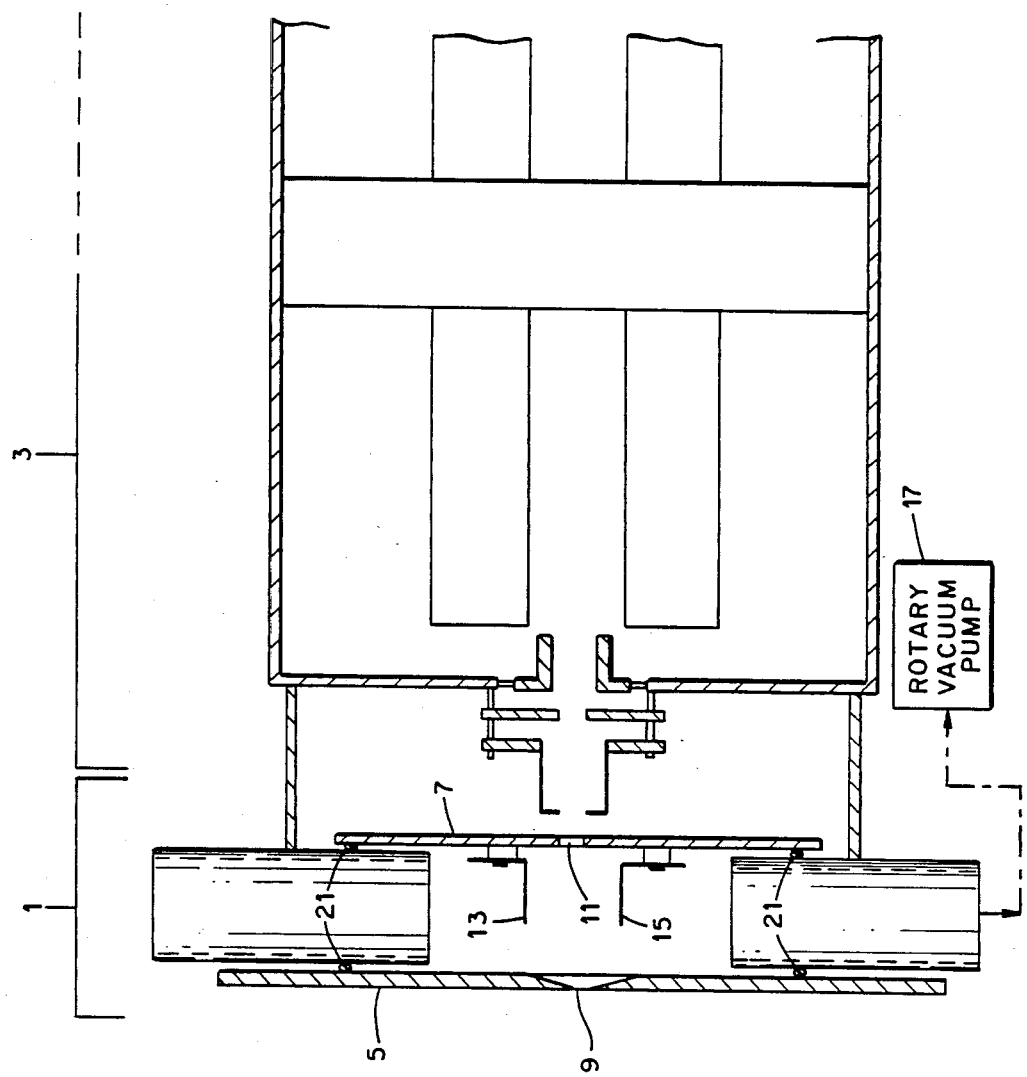
FIG. 1 is a top plan view of an atmospheric sampling glow discharge ionization device connected to a mass spectrometer.

Referring to FIG. 1, an ionization chamber 1 is connected to a quadruple mass spectrometer 3. Primary plates 5 and 7 have a circular inlet aperture 9 having a diameter of 200 $\mu$m and a circular outlet aperture 11 having a diameter of 800 $\mu$m, respectively. Both the inlet aperture 9 and the outlet aperture 11 are aligned with the sample path of the mass spectrometer 3. The sample path is defined as the path that the sample travels in passing through the ionization chamber and analyzer. The ionization chamber communicates with a gaseous sample contained in the atmosphere by means of the inlet and communicates with an analyzer by means of the outlet.

A secondary plate 13 and a secondary plate 15 are spaced substantially parallel to each other and mounted on the primary plate 7 on opposite sides of the outlet aperture 11. The distance between the secondary plate 13 and the secondary plate 15, as shown in FIG. 1, is about 1.5 centimeters. The secondary plates 13 and 15 are disposed on opposite sides of and substantially equidistant from the sample path.

A voltage difference is applied in a conventional manner across at least one set of parallel plates in such a way that a glow discharge is induced between the electrodes.

The pressure in the ionization chamber is lowered to a range of between about 0.1 and 1 torr by a 15 liter per second rotary vacuum pump 17. The mass spectrometer 3 is maintained at a pressure in the range from about $10^{-4}$ to about $10^{-5}$ torr, preferably about $5 \cdot 10^{-5}$ torr.

Ambient air is drawn in through the inlet aperture 9 by the vacuum and encounters the voltage difference created within the ionization chamber 1. The gaseous molecules contained in the ambient air are then ionized by the glow discharge produced by the voltage difference and directed through the outlet aperture into the mass spectrometer 3.

In one embodiment a glow discharge for forming ions is established with the primary plates 5 and 7 serving as the electrodes. A voltage difference between the primary plates 5 and 7 of between about 350 and 400 volts is sufficient for a glow discharge to occur. The distance between the primary plates 5 and 7, as shown in FIG. 1, is about 2 centimeters and is not particularly critical. In this embodiment, the secondary plates 13 and 15 are held at the same potential, usually about 0 volts.

The best results are obtained when the negative glow of the discharge is nearest to the primary plate 5. This situation is established when the primary plate 5 serves as the cathode and the primary plate 7 serves as the anode. Ions which are formed in the discharge and pass through the outlet aperture 11 are focused into the mass spectrometer 3, detected and subsequently massanalyzed.

To optimize the performance of the mass spectrometer in terms of transmission and mass resolution, the primary plate 5 is normally held at between about −350 and −400 volts, and the primary plate 7 is held at about −8 volts when negative ion analysis is desired and at about +8 volts when positive ion analysis is desired.

In an alternate embodiment for forming ions, a glow discharge is established between the secondary plates 13 and 15. In this embodiment, the voltage on one primary plate 5 has very little effect on the data while the voltage on the other primary plate 7 is varied to optimize the extraction of ions from the discharge, thereby optimizing the performance of the mass spectrometer. The potentials on the secondary plates 13 and 15 are each about 200 volts and are of opposite polarity.

The secondary plate glow discharge embodiment is preferred for analyzing positive ions, whereas the primary plate glow discharge embodiment is preferred for analyzing negative ions.

Figure 2:
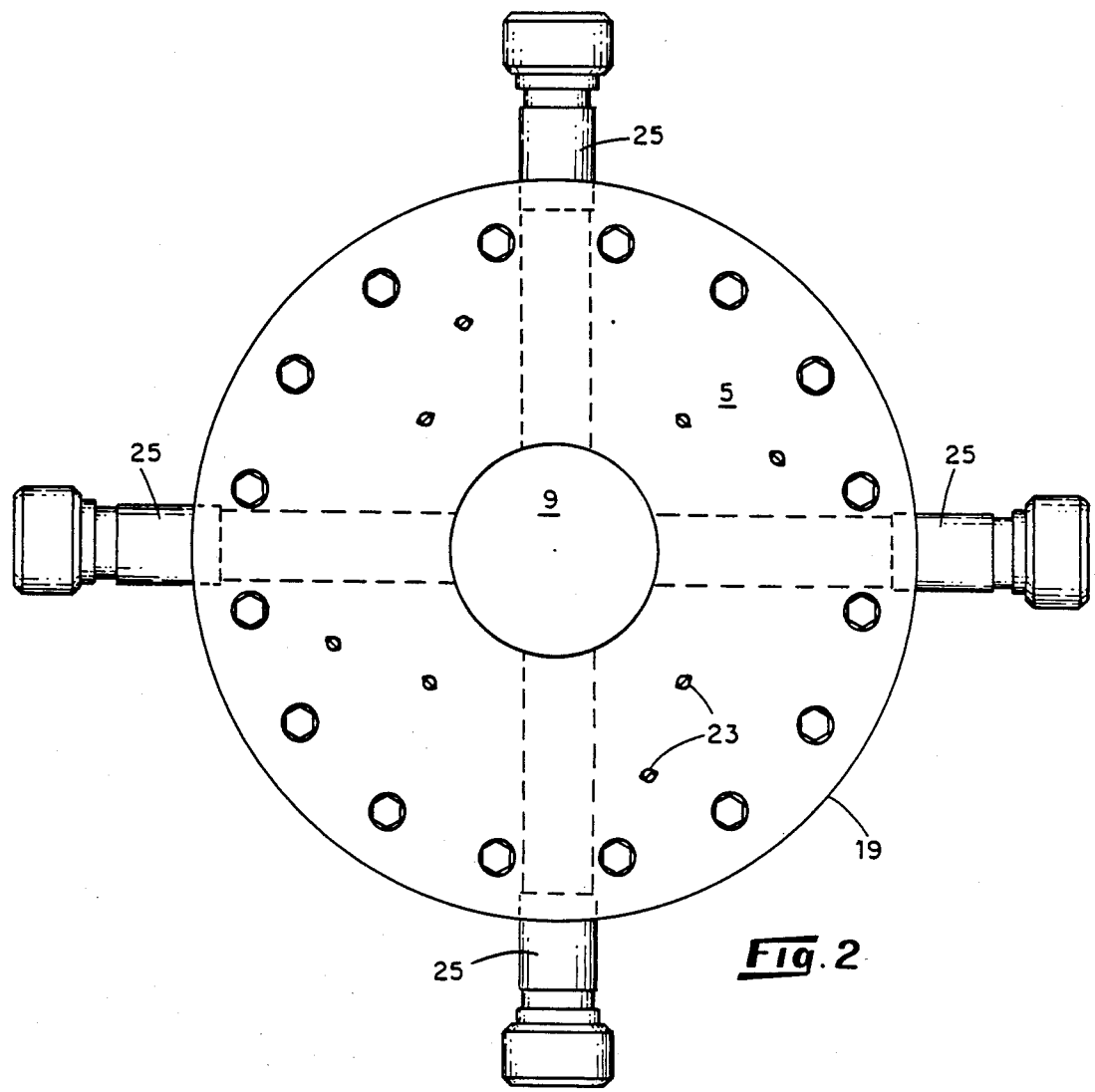
FIG. 2 is a front elevational view showing a support flange for use in the atmospheric sampling glow discharge ionization source.
Figure 3:
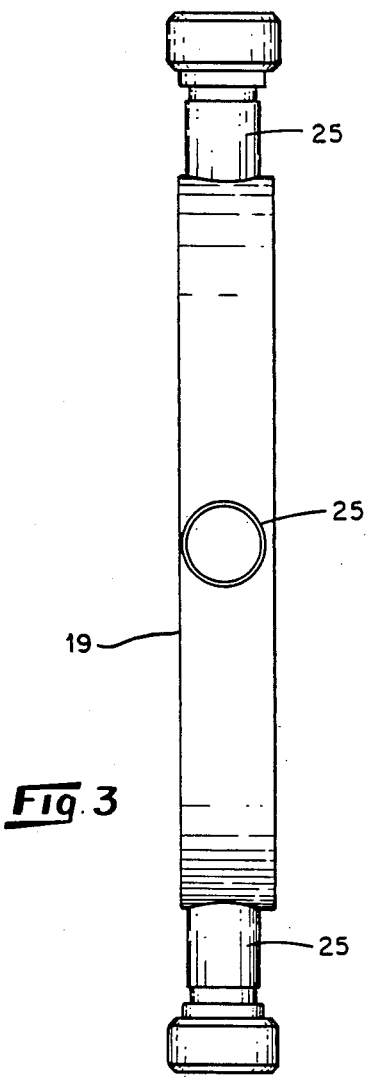
FIG. 3 is a side elevational view of the flange shown in FIG. 2.

Referring to FIGS. 2 and 3, the atmospheric sampling glow discharge ionization source is constructed with a 6-inch outer diameter support flange 19 that is apertured for drawing a vacuum. A suitable flange is sold by MDC Vacuum Products Corp. of Hayward, California, under the trademark CONFLAT ™.

The primary plate 5 having the inlet aperture 9 is attached to the outside face of the flange 19. An O-ring seal 21 is used for the vacuum seal and also to electrically isolate the primary plate 5 from the flange 19. Nylon screws 23 are used to attach the primary plate 5 to the flange 19 in order to maintain electrical isolation. The primary plate 7 having the outlet aperture 11 is attached to the vacuum side of the flange 19 in a like manner. There is a 1.75 inch diameter hole through the center of the flange 19 which is in the region where the glow discharge, and thus ionization, occurs. The diameter of this hole is not critical.

Pump-out ports 25 have been drilled through the side of the flange 19. In one preferred embodiment, the system has four such ports. However, as illustrated in FIG. 2, up to 16 or more ports are possible. The number of ports is a function of the magnitude of vacuum desired and the available surface area. By using more pumping ports, greater pumping speed can be obtained and thus the inlet aperture 9 can be enlarged, thereby increasing the amount of gaseous sample entering into the discharge region.

Alternate embodiments include a molecular beam-type arrangement where a glow discharge is set up between an orifice plate and skimmer or between the skimmer and a subsequent electrode. This embodiment allows for a larger sampling aperture, which should provide more sample and thus greater sensitivity. Similar improvements are possible in the design shown in FIG. 1 by using a larger inlet aperture 9 and increasing the vacuum pumping in the region between the primary plates 5 and 7.

In a further embodiment, the number of sample molecules introduced into the discharge can be increased by increasing the diameter of the inlet aperture still further and using a semi-permeable membrane over the inlet aperture which is more permeable to organic molecules than to oxygen and nitrogen. The membrane would then, in effect, reduce the pumping requirements. Additionally, a screen can be used to support the membrane and serve as an electrode.

Another embodiment also includes a double mass spectrometer configuration, whereby both positive and negative ions can be sampled simultaneously. Since many chemical species are detected with much greater sensitivity in one mode relative to the other, such a dual mass spectrometer arrangement can facilitate realtime monitoring of a wider variety of compounds than is possible using one mode at a time.

Relative concentrations of the adduct ions depend, of course, on the relative humidity. There are roughly 104 collisions per ion during the ion source residence time. When the sample molecule has a higher proton affinity or electron affinity than the neutral counterparts to the reagent ions, the charge will be transferred to the sample. Due to the many collisions in the source, the charge tends to accumulate in the most stable ions.

The atmospheric sampling glow discharge ionization source is operated at pressures approximately three orders of magnitude lower than API sources. The less stable ions are therefore discriminated against less severely than with sources where true thermal and chemical equilibrium re obtained. The kinetics of ion formation also contribute to this decreased discrimination. Additionally, the relatively low pressure of the atmospheric sampling glow discharge ionization source reduces the probability of ion-ion recombination and also tends to reduce the amount of clustering.

There are at least $10^{10}$ more primary ionizing electrons in the atmospheric sampling glow discharge ionization source than in API sources which use beta emitters to provide the primary ionizing electrons. This overwhelming abundance of primary ionizing electrons provides an increase in the dynamic range since the ionization in the atmospheric sampling glow discharge ionization source is not limited by the amount of primary ionizing electrons, and thus ionization saturation does not occur even at relatively high sample concentrations. Discrimination in ionization, which may occur in conventional API sources when two contaminants are present in widely varying concentrations, is also reduced by atmospheric sampling glow discharge ionization sources for similar reasons.

When compared to API sources which use a corona discharge occurring at atmospheric pressure, the atmospheric sampling glow discharge ionization source can operate for substantially longer periods of time before maintenance is required. This factor is important for both remote monitoring systems and continuously operating systems.

The atmospheric sampling glow discharge ionization technique has demonstrated higher sensitivity than either type of API source for the compounds studied. True sensitivity comparisons for the sources cannot be made when different mass spectrometers and detectors are used. However, laboratory tests have been performed comparing a beta emitter API source with the atmospheric sampling glow discharge ionization source of the present invention. For the compounds studied, the atmospheric sampling glow discharge ionization source provides detection limits from about two to three orders of magnitude lower than the API source.

Another comparison is obtained by comparing the results of the present invention with the best results reported from API techniques in the literature. For a solid sample of 2,4,6-TNT as described above, an API mass spectrometer in the negative ion mode obtains a molecular anion signal of about 30,000 counts per second with a background count rate of about 1,000 counts per second. In contrast, for a solid TNT sample held near the aperture of the present invention, in the negative ion mode and set at the same mass resolution indicated in the published account, the present invention obtains a molecular ion signal of about 400,000 counts per second with a background of about 200 counts per second. The background count rates are high in both cases and could be reduced by conventional instrument signal optimization techniques. The absolute signal strengths indicate that the atmospheric sampling glow discharge ionization is on the order of ten times more sensitive to TNT than the corona discharge API source.

The use of differential pumping and creation of a vacuum in the atmospheric sampling glow discharge ionization source enables the use of larger apertures than in conventional API sources, thus reducing the chances of the aperture clogging and also making unnecessary the addition of a complex "gas curtain".

The atmospheric sampling glow discharge ionization source can be used as an ion source for virtually any type of mass spectrometer in the analysis of most gaseous organic compounds in ambient air. Several areas of particular interest are, for example, the detection of vapors from explosive compounds, vapors from flammable liquids, and chemical warfare agents. This ionization source is also useful in systems designed to monitor air pollutants or to screen for hazardous chemical wastes.

Further understanding of the invention may be gained from consideration of the following examples which are submitted to be merely illustrative of the invention and not to limit its scope.

EXAMPLE 1

Detection of 2,4,6-TNT in simulated ambient air:

A voltage difference of approximately 400 volts is applied to primary plates 5 and 7 of an ionization chamber as described above. The pressure in the ionization chamber is reduced by application of a vacuum. The voltage application will spontaneously initiate a glow discharge at a source pressure of 0.93 millibar with a typical discharge current of 1 milliamp.

Ambient air containing a gaseous sample of 2,4,6-TNT is simulated by placing a small vial or jar containing 2,4,6-TNT at the end of a short length of ¼ inch O.D. stainless steel tubing and butting up the other end against the inlet aperture 9. The tubing provides for the sampling of the head space vapor over the 2,4,6-TNT in the vial thus directing the gaseous sample towards the glow discharge source.

The gaseous 2,4,6-TNT molecules passing through the inlet are ionized upon contact with the glow discharge. The ionized particles are directed through the outlet and into a mass spectrometer to the detector. The various focusing controls are adjusted in a conventional manner to maximize the signal reaching the detector, keeping the resolution of the mass spectrometer at unity. In addition to focusing the mass spectrometer, the voltage difference between the two electrodes of the glow discharge is adjusted to maximize the signal intensity.

EXAMPLE 2

The procedure of Example 1 is repeated except that voltage is applied to secondary plates 13 and 15 to induce ionizing glow discharge, and instead of drawing the gas sample through the stainless steel tube, the open vial of 2,4,6-TNT is simply held near the ionization chamber inlet so that sample vapors may be drawn into the inlet.

While several embodiments of the invention have been described, it will be understood that it is capable of still further modification, and this application is intended to cover any variations, uses, or adaptations of the invention following the general principles of the invention and including such departures from the present disclosure falling within the limits of the appended claims and equivalents thereof.

What is claimed is:

1. Apparatus for analyzing gaseous chemicals in the atmosphere comprising an ionization chamber and an analyzer which operates under vacuum, said ionization chamber defining an inlet and an outlet, said inlet communicating with the atmosphere for admitting an atmospheric gaseous sample to be analyzed, said outlet communicating with said analyzer, at least one pair of spaced electrodes disposed in said chamber proximate to a sample path leading from said inlet to said outlet, means for establishing a glow discharge between said electrodes, and means for maintaining said chamber at a pressure below atmospheric pressure.

2. Apparatus according to claim 1, wherein said means for establishing a glow discharge applies a voltage difference in the range from about 350 to 400 volts between said electrodes.

3. Apparatus according to claim 1, wherein said one pair of electrodes comprises two primary plates spaced apart and substantially parallel to each other, one of said primary plates having an opening therein defining said inlet and the other of said primary plates having an opening therein defining said outlet; and wherein said inlet and said outlet of said ionization chamber are linearly aligned with a sample path in said analyzer.

4. Apparatus according to claim 3, wherein said inlet has a diameter of about 200 $\mu$m; said outlet has a diameter of about 800 $\mu$m; and said primary plates are spaced apart a distance equal to about 2 centimeters.

5. Apparatus according to claim 3, further comprising a pair of secondary electrodes for analyzing positive ions, said secondary electrodes comprising two secondary plates spaced apart and substantially parallel to each other, said secondary plates being disposed between said primary plates and on opposite sides of and substantially equidistant from said sample path, said secondary plates being spaced apart a distance equal to about 1.5 centimeters.

6. Apparatus according to claim 1, wherein said means for maintaining said chamber at a pressure below atmospheric pressure provides a pressure in the range of from about 0.1 to about 1 torr.

7. Apparatus according to claim 6, wherein said means for maintaining said chamber at a pressure below atmospheric pressure comprises a rotary vacuum pump.

8. Apparatus according to claim 1, wherein said analyzer is a mass spectrometer.

9. Apparatus according to claim 8, wherein said mass spectrometer operates at a pressure from about $10^{-4}$ to about $10^{-5}$ torr.

10. Apparatus according to claim 5, wherein a voltage difference is applied between said primary plates to the exclusion of said secondary plates, said primary plate having the opening defining the inlet being a cathode and said primary plate having the opening defining the outlet being an anode, said cathode having a potential of between about negative 350 volts and negative 400 volts and said anode, when negative ion analysis is desired, having a potential of about negative 8 volts and when positive ion analysis is desired having a potential of about positive 8 volts.

11. Apparatus according to claim 5, wherein a voltage difference is applied between said secondary plates to the exclusion of said primary plates, the potential at one of said secondary plates being about +200 volts and the potential at the other of said secondary plates being about −200 volts, when positive ion analysis is desired.

12. A method for analyzing gaseous chemicals in the atmosphere comprising the steps of:
   (a) providing an ionization chamber defining an inlet and an outlet, said inlet communicating with the atmosphere for admitting an atmospheric gaseous sample to be analyzed, said outlet communicating with an analyzer which operates under vacuum, said chamber having disposed therein at least one pair of spaced electrodes proximate to a sample path leading from said inlet to said outlet;
   (b) maintaining the interior of said ionization chamber at subatmospheric pressure;
   (c) applying a voltage difference across said electrodes to induce a glow discharge between said electrodes;
   (d) admitting said atmospheric gas sample containing molecules to be analyzed through said inlet into said chamber, ionizing said molecules to be analyzed in said glow discharge, and directing the ionized molecules through the outlet and into the analyzer; and
   (e) analyzing the ionized molecules in said analyzer.

13. A method according to claim 12 wherein said one pair of electrodes comprises two primary plates spaced apart and substantially parallel to each other, one of said primary plates having an opening defining said inlet and the other of said primary plates having an opening defining said outlet, and wherein said voltage difference is in the range from about 350 to about 400 volts.

14. A method according to claim 13, wherein said ionization chamber further comprises a second pair of electrodes for analyzing positive ions, said electrodes comprising two secondary plates spaced apart and substantially parallel to each other, said secondary plates being disposed between said primary plates and on opposite sides of and substantially equidistant from said sample path.

15. A method for analyzing gaseous chemicals in the atmosphere comprising the steps of:
   (a) providing an ionization chamber defining an inlet and an outlet, said inlet communicating with the atmosphere for admitting an atmospheric gaseous sample to be analyzed, said outlet communicating with an analyzer which operates under vacuum, said chamber having disposed therein at least one pair of spaced electrodes proximate to a sample path leading from said inlet to said outlet;
   (b) maintaining the interior of said ionization chamber at subatmospheric pressure;
   (c) applying a voltage difference across said electrodes to induce a glow discharge between said electrodes;
   (d) admitting said atmospheric gas sample containing molecules to be analyzed through said inlet into said chamber, ionizing said molecules to be analyzed in said glow discharge, and directing the ionized molecules through the outlet and into the analyzer; and
   (e) analyzing the ionized molecules in said analyzer.

16. A method according to claim 12, wherein said analyzer is a mass spectrometer.

17. A method according to claim 14, wherein said voltage difference is applied between said primary plates to the exclusion of said secondary plates, said one primary plate having the opening defining the inlet being a cathode and said other primary plate having the opening defining the outlet being an anode.

18. A method according to claim 17, adapted for negative ion analysis wherein said cathode has a potential of between about negative 350 volts and negative 400 volts and said anode has a potential of about negative 8 volts.

19. A method according to claim 17, adapted for positive ion analysis wherein said cathode has a potential of between about negative 350 volts and negative 400 volts and said anode has a potential of about positive 8 volts.

20. A method according to claim 14, wherein said voltage difference is applied between said secondary plates to the exclusion of said primary plates, and wherein the potential at one of said secondary plates is about +200 volts and the potential at the other of said secondary plates is about +200 volts.

* * * * *

UNITED STATES PATENT AND TRADEMARK OFFICE
CERTIFICATE OF CORRECTION

PATENT NO. : 4,849,628

DATED : July 18, 1989

INVENTOR(S) : Scott A. McLuckey, et al

It is certified that error appears in the above-identified patent and that said Letters Patent is hereby corrected as shown below:

Col. 10, line 51, delete "+200" and insert -- -200 --.

Signed and Sealed this

Twenty-seventh Day of April, 1993

Attest:

MICHAEL K. KIRK

*Attesting Officer*  *Acting Commissioner of Patents and Trademarks*